(12) United States Patent
Dreese et al.

(10) Patent No.: US 7,449,209 B2
(45) Date of Patent: Nov. 11, 2008

(54) METHOD AND INGREDIENT FOR INCREASING SOLUBLE FIBER CONTENT TO ENHANCE BILE ACID BINDING, INCREASE VISCOSITY, AND INCREASE HYPOCHOLESTEROLEMIC PROPERTIES

(75) Inventors: Patrick C. Dreese, Plymouth, MN (US); Alicia A. Perdon, Maple Grove, MN (US); Daniel J. Lewandowski, Bloomington, MN (US); David W. Plank, Taylors Falls, MN (US); Fred Hemker, Maple Grove, MN (US); Richard H. Fanning, New Hope, MN (US)

(73) Assignee: General Mills IP Holdings II, LLC, Minneapolis, MN (US)

( * ) Notice: Subject to any disclaimer, the term of this patent is extended or adjusted under 35 U.S.C. 154(b) by 260 days.

(21) Appl. No.: 10/207,601

(22) Filed: Jul. 29, 2002

(65) Prior Publication Data

US 2004/0018256 A1    Jan. 29, 2004

(51) Int. Cl.
*A23L 1/10* (2006.01)
(52) U.S. Cl. .............. 426/615; 426/478; 426/479; 426/481; 426/482; 426/618
(58) Field of Classification Search ............. 426/615, 426/618, 478, 479, 481, 482
See application file for complete search history.

(56) References Cited

U.S. PATENT DOCUMENTS 5,023,103 A * 6/1991 Ramaswamy ............ 426/626
5,510,337 A    4/1996 Aritsuka ..................... 514/57
5,766,662 A * 6/1998 Inglett ......................... 426/481
5,817,381 A    10/1998 Chen et al. ................ 428/34.8
6,083,582 A    7/2000 Chen et al. ................ 428/34.8
6,261,629 B1    7/2001 Mazza et al. .............. 426/656
6,262,629 B1    7/2001 Stengel et al. .......... 330/124 R
6,482,430 B1 * 11/2002 Weightman et al. ......... 424/441

FOREIGN PATENT DOCUMENTS

JP    59-102 360    6/1984
WO    98/31713 A1    7/1998

OTHER PUBLICATIONS

Vacuum 2002 for Food Storage, 2001.*
Newman, et al., "Growth and lipid metabolism as affected by feeding of hullless barleys with and without supplemental β-glucanase," *Plant Foods for Human Nutrition*, 41: 371-380, 1991.

* cited by examiner

*Primary Examiner*—Lien Tran
(74) *Attorney, Agent, or Firm*—John A. O'Toole; Douglas J. Taylor; Peter Dardi

(57) ABSTRACT

The present invention relates to a method for modifying materials that have low soluble fiber content and high insoluble fiber content so as to enhance bile acid binding capacity by increasing the level of available soluble fiber that can be obtained from such starting materials in order to create ingredients that are useable in food intermediates that are suitable for lowering unhealthy cholesterol levels. More particularly, the present invention relates to controlling the moisture content, mechanical pretreatment and alkali treatment of such starting materials as wheat bran or shorts.

25 Claims, No Drawings

METHOD AND INGREDIENT FOR INCREASING SOLUBLE FIBER CONTENT TO ENHANCE BILE ACID BINDING, INCREASE VISCOSITY, AND INCREASE HYPOCHOLESTEROLEMIC PROPERTIES

CROSS-REFERENCES TO RELATED APPLICATIONS

None.

BACKGROUND OF THE INVENTION

The present invention relates to a method for modifying cereal or grain based materials that have low soluble fiber content and high insoluble fiber content so as to enhance bile acid binding capacity by increasing the level of available soluble fiber that can be obtained from such starting materials as well as the viscosity in order to create ingredients that are useable in food intermediates that are suitable for lowering unhealthy cholesterol levels. More particularly, the present invention relates to a process for controlling a number of parameters such as temperature and moisture content as well as providing for such other steps as the mechanical pretreatment and alkali treatment of grain or cereal based starting materials, including but not limited to wheat bran or shorts.

The present invention is related to a novel component for use in a food intermediate intended for incorporation into a consumer food product. More specifically, the ingredient or component, provided either alone or acting synergistically with other select ingredients is part of an ingestible food product intended for human or animal consumption that provides a health benefit. The food component provides beneficial hypocholesterolemic activity through increased bile acid binding activity and increased viscosity while simultaneously delivering a food product, which is not adversely affected by the inclusion of the modified bran product, either in taste or texture or in any undesirable side effects.

There is a large amount of information in circulation today concerning elevated cholesterol levels and the health consequences due to that condition. In an effort to combat this result, a number of pharmaceutical applications, dietary supplements and other solutions relating to the treatment of high cholesterol levels have been previously introduced. However, regrettably, many of these products have unpleasant attributes, such as mouth feel, that is they can feel slimy or sticky, have a displeasing taste or result in undesirable side effects which diminishes their overall value to the intended end user.

In addition, there also appears to be a growing disdain against ingesting some sort of dietary supplement, pharmaceutical treatment or other product to attain some perceived beneficial effect from such products. This may be due to a growing reliance on pills or tablets to sustain or maintain our health. The growing dependence on supplements may also surprisingly contribute to malnutrition as other valuable. vitamins and minerals can be omitted or overlooked when too much focus is diverted to certain items. Moreover, certain supplements may actually remove valuable macronutrients and micronutrients from the system. Individuals may also be concerned with potential risks and side effects associated with certain medications, treatments or supplements. In fact, dietary restrictions and other health concerns may preclude certain portions of the population from even consuming such products. As such, there remains a continuing interest in developing good tasting, well balanced, food products that contribute to a well balanced diet as well as provide a vehicle by which to deliver the benefit of cholesterol reduction in a palatable and efficient manner to meet the changing needs of the population.

Cholesterol in humans is known to come from primarily two sources, the body's own production of cholesterol (endogenous) and dietary cholesterol (exogenous). Lipoproteins contain specific proteins and varying amounts of cholesterol, triglycerides and phospholipids.

Bile acids are synthesized from cholesterol in the liver and then secreted into the intestines. Reducing the level of bile acid reabsorption facilitates the maintenance of a healthy cholesterol level. One method for reducing bile acid reabsorption is achieved by increasing the gut viscosity. Alternatively, a non-digestible dietary component which binds bile acids secreted in the proximal jejunum will reduce bile acid reabsorption in the lower intestines (distal ileum).

There are three major classes of lipoproteins and they include very low-density lipoproteins ("VLDL"), low-density lipoproteins ("LDL") and high density lipoproteins ("HDL"). The LDLs are believed to carry about 60-70% of the serum cholesterol present in an average adult. The HDLs carry around 20-30% of serum cholesterol with the VLDL having around 1-10% of the cholesterol in the serum. To calculate the level of non-HDL cholesterol present (find the level of LDL or VLDL levels), which indicates risk; the HDL is subtracted from the total cholesterol value.

Typically, the average person consumes between 350-400 milligrams of cholesterol daily, while the recommended intake is around 300 milligrams. Increased dietary cholesterol consumption, especially in conjunction with a diet high in saturated fat intake, can result in elevated serum cholesterol. Having an elevated serum cholesterol level is a well-established risk factor for heart disease and therefore there is a need to mitigate the undesired effects of cholesterol accumulation. High cholesterol levels are generally considered to be those total cholesterol levels at 200 milligrams and above or LDL cholesterol levels at 130 milligrams and above. By lowering the total system LDL cholesterol level, it is believed that certain health risks, such as coronary disease and possibly some cancers, that are typically associated with high cholesterol levels, can be reduced by not an insignificant amount.

Numerous studies relating to modifying the intestinal metabolism of lipids have been done to illustrate that such effects can reduce a high cholesterol level. Hampering the absorption of triglycerides, cholesterol or bile acids or a combination of these items results in a lowering of cholesterol levels in the serum.

Soluble fiber typically remains undigested, except by colonic microflora present in the lower intestines. Soluble dietary fiber is believed to have a beneficial effect in the reduction of high serum cholesterol levels and reducing the risk associated with such elevated levels. In addition, soluble dietary fiber can have the additional beneficial effect of reduced constipation and improved regularity. However, too much fiber in the diet can create undesirable gastrointestinal side effects such as flatulence, diarrhea, and abdominal cramps, etc. leading consumers to stay away from food products that contain too much dietary fiber, regardless of any associated health benefits. While some consumers may not completely avoid such products, they also do not typically regularly use such products due to the problems enumerated above or alternatively, or in combination due to the unpleasant taste of such products. This illustrates some of the problems with prior solutions that were aimed at providing high fiber diets directed at lowering cholesterol levels, and highlights the need to create a more balanced solution that fits not only within more normal dietary patterns but also meets consumer demand for better tasting, healthy products.

Another difficulty with many of the prior art solutions, regardless of whether they are successful in lowering cholesterol levels or not, is simply a matter of the cost of the ingredients or components which are needed to achieve the desired benefit. Only a very small segment of the population may be willing to pay eight or even ten dollars for a box of cereal or a loaf of bread, despite the benefit associated with it. In addition even if consumers purchase such a product initially, the high cost is likely to be more of a disincentive to purchase the product in the future, when compared with the incentive of the health benefit associated with the product.

A still further issue associated with such prior art food problems is that the consumer may be forced to eat several servings of the food product in order to attain the benefit of cholesterol reduction. This further complicates the delivery of the health benefit to the consumer in that a consumer may not want to eat a half a loaf of bread or consume three or more bowls of cereal at a meal. Moreover, over consumption can lead to other problems such as weight gain.

There have been previous attempts to increase the level of soluble fiber from sources that are high in insoluble fiber, however such prior methods have relied heavily on hydrating the resultant materials such that the material has a moisture content of around 95% and a solid content of approximately 5%. However, this creates a sticky or slimy mass that has a tendency to gel and is very difficult to handle. In addition, such prior processes generally extract only about 30 percent by weight of useable components from the initial starting source, and even a significantly lower amount of soluble fiber (usually less than four or five percent) creating a lot of waste through loss of solids and expense in evaporating water.

Another concern created by the extraction of fiber via such known methods is that the prior art processes create a lot of waste material in discarding the hulls and other portions of the crops. In addition, potentially less expensive sources of fiber are overlooked due to the fact that there is such a low level of soluble fiber present in such sources.

As such, what is needed is a process for increasing the recovery of soluble fiber from known sources or sources which do not economically prejudice the resulting food intermediate or food product and using the recovered fiber in the provision of food products that provide beneficial hypocholesterolemic activity.

BRIEF SUMMARY OF THE INVENTION

The present invention will now be described by reference to the following embodiments, which are not intended to be limiting in scope.

In one embodiment of the present invention, a method of increasing soluble fiber levels and viscosity in grain or cereal based components that are suitable for use in food intermediates is described and comprises the steps of, initially providing a source of material having an initial extractable soluble fiber content of less than 4% by weight on a dry weight basis. Next, the material is hydrated to a moisture content of 40-60% and then an alkali is added to the material to create a mixture. The mixture may or may not be subjected under vacuum before further processing. The mixture is then cooked, such as through steaming under pressure. The moisture content of the material may be manipulated during such cooking. The mixture is then neutralized through the addition of an acid and then dried to less than 20% moisture content. Finally, the mixture is ground to form a powder having an extractable soluble fiber content of greater than 8% by weight.

In a further embodiment of the present invention, a cereal based material for use as an ingredient for use in preparing a food intermediate having improved bile acid binding capacity and viscosity is described and comprises, a first material having a particle size of greater than 10 microns. The first material has an initial level of extractable soluble fiber. An alkali selected from a group of calcium hydroxide, sodium hydroxide and potassium hydroxide, a hydrating agent and a neutralizing agent are mixed with the first material. The first material after addition of the alkali, hydrating agent and neutralizing agent creates a second material that has a second level of extractable soluble fiber. The second material level of extractable soluble fiber from the second material is at least 50% greater than the first level of extractable soluble fiber of the first material.

The powder obtained from the forgoing process or the material can be used as an ingredient in the preparation of food intermediates such as dough as well as in the preparation of ready to eat meals, ready to eat cereals, snacks and baking product such as breads, muffins, baking mixes and the like.

This and other objects of the invention will become clear from an inspection of the detailed description of the invention and from the appended claims

DETAILED DESCRIPTION OF THE INVENTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

The soluble fiber component of the present invention can be derived from a wide variety of grains, cereals or components thereof and are composed of polysaccharides having a variety of structures. Examples of such grains or cereals include wheat, rice, corn, oats, barley and the like. As indicated above, soluble fiber is generally resistant to human digestive enzymes, except for colonic microflora present in the lower intestines, and is known for its water and ion-binding capacity. Obtaining an enhanced level of soluble fiber is an aim of the present invention.

Handling of viscous soluble fibers is normally difficult due to the fact that the fiber has high viscosity. Surprisingly, applicants have discovered that by performing the modification as described herein where the solids content of the bran ranges from between 40 to 60% by weight and more preferably between 45% to 55% by weight, significant improvement in the conversion to soluble fiber can be obtained over prior art solutions. If the moisture content falls outside of this narrow window, applicant's have found that the material is either too sticky or slimy due to high water content or in the alternative there isn't sufficient moisture in the product which creates other handling difficulties. Following are exemplary sources of soluble fiber material.

Psyllium, is a known mucilaginous material derived from seeds from the plants of the *Plantago* genus, *Plantago ovata*, found in sub-tropical areas. The seeds are dark and shiny and have something of a concave shape to the exterior. Psyllium has been regularly used as a laxative to promote regular bowel function. Psyllium seed may be used in ground, dehusked or in whole form and represents a source of soluble dietary fiber. However, psyllium can have a coarse or rough texture making ingestion occasionally difficult, if the fiber component is not processed in a manner making it readily useable in a consumer food product.

Oat flour is essentially heat-treated oat groats (hulled, crushed oats) or rolled oats that are ground on a hammer mill or other machine. There is no separation of the components during the processing of the flour.

Oat bran is produced by grinding clean oat groats or rolled oats and separating the resulting flour by suitable means, such as sieving, into fractions such that the oat bran fraction is not more then 50% of the original starting material.

Wheat bran is produced by grinding or milling clean wheat and then separating the resulting flour by suitable means, such as sieving, into fractions. Regular wheat bran has only about 2.5% soluble fibers. Wheat bran is relatively inexpensive and generally less than about $0.02/per pound.

Barley, is processed in a manner that resembles the procedure as set forth above, in that it consists of cleaning, hulling, sieving and then grinding. Waxy hulless barley has a higher dietary fiber content than most other sources of fiber and can range from 14 to 20% of the dry weight.

Wheat shorts, as used herein, refers to a product or grain that cannot be cleanly separated into bran, germ or endosperm. Wheat shorts are made up of a substantial portion of wheat bran and contain about 40% fiber of which more than half is arabinoxylan. Wheat shorts are available in large quantities and roughly at about $0.02/pound. Wheat shorts as used in the present invention are available from General Mills, Inc. Minneapolis, Minn. Wheat shorts are often by-products of the milling industry.

The starting material of the present invention are generally selected from the group of milling by-products or other grains or components thereof which do not create an economic burden or disincentive to their inclusion into the food intermediate or food product being produced in accordance with the present invention. In one embodiment of the present invention, wheat bran is selected for illustration in the following example. It should however be understood that oat bran, rice bran and corn bran may be used in connection with the present invention. In addition, the starting material may also comprise a mixture of two or more of wheat bran, oat bran, corn bran or rice bran.

The soluble fiber content of regular wheat bran is approximately 2.2% on a dry weight basis. Wheat shorts, oat hulls, corn cobs and other sources having high levels of insoluble fiber material may also be used instead of wheat bran as a starting material.

It has been found that through the treatment of wheat bran with enzymes (cellulases and xylanases) the soluble fiber content can be increased by about 100% to approximately 4.4% on a dry weight basis. However, more significant improvement in increasing the soluble fiber content can be obtained by treatment with alkali, steaming (in the presence or absence of a vacuum) and grinding the material into a very fine powder. While 15% soluble fiber on a dry weight basis has been achieved on a number of occasions, greater than 8% and 10% are usual and more particularly 11% soluble fiber content is the more typical amount obtained from the starting material. In addition, achieving levels of 15% or more through the process described herein can yield a soluble fiber that has a bitter flavor or is discolored and which may not be suitable in as broad a range of applications as other levels of ingredients.

It has been surprisingly discovered, that by increasing the soluble fiber content of the starting material through the process described in the present invention a reduction of up to 25% of the cholesterol level of hamsters can be obtained through use of the modified bran obtained by the process of the present invention over untreated or unmodified bran.

In one embodiment of the present invention, the wheat bran is modified by treatment with heat (steaming), water and alkali. The amount of water suitable for use in the present invention ranges from approximately 20% to in excess of 2500% of the weight of the bran. Generally, however, it is preferred to use an amount of water that is equal to or less than the dry weight of the bran, or 30 to 100% of the dry weight basis of the bran.

Calcium hydroxide (CaOH), due to its additional nutritional value (increasing calcium level) and cost, is the preferred alkali, however other hydroxides are also suitable for use in the present invention, including but not limited to sodium hydroxide (NaOH) and potassium hydroxide (KOH). In practicing the present invention the amount of calcium hydroxide ranges from roughly 1% to 10%, with the preferred amount being approximately 3-8% and more preferably about 4-8% dry weight of the bran. After the addition of the alkali, additional water may be added to maintain the moisture level to between 40% to 60% and more preferably to between 45% to 55%.

In one working example for the present invention, the dry ingredients, wheat bran (approximately 90-98% on a dry weight basis in this example is 10 pounds) and calcium hydroxide (2-10% on a dry weight basis and approximately 0.8 pounds for this exemplary process) are mixed together are then added into the cooker. The cooker has an initial shell temperature of around 70-75° F.

The wheat bran is then steamed/cooked at atmospheric pressure or alternatively, cooked in a pressurized vessel. In the present embodiment, the heating/steaming is done for a total time range of between 10 to 120 minutes with approximately 40 to 60 minutes being preferred. For the present example, the heating/steaming is done in three stages or durations of 10 minutes, 10 minutes and 20 minutes. During the heating/steaming, the pressure in the vessel is maintained at around 25 to 36-psig. The cooking/steaming temperature ranges from between 100° C. to 140° C. and more preferably from about 130° C. to 138° C. and the heating/steaming is done in a batch cooker designed and used in the production of ready to eat ("RTE") cereals. The contents are then discharged from the cooker. The batch after removal from the cooker had a moisture content of approximately 46%.

After the cooking step (the heating/steaming), the ingredients are mixed in a Hobart mixer. Citric acid is then added to neutralize the bran during the mixing Hydrochloric acid may also be used. In the present embodiment approximately 0.82 grams of citric acid is used for roughly each gram of alkali (calcium hydroxide) that was added. The cooked neutralized bran is then dried for twenty minutes at a temperature of 200°-210° F. to obtain a moisture content of less than 20% and preferably to about 12% by moisture. The dried bran is then allowed to equilibrate overnight and is then ground to a powder with a mill.

To maintain an adequate moisture level for the present invention, the ratio of bran to water to alkali (calcium hydroxide) as provided in the present example is approximately 1 to 0.3-0.5 to 0.03-0.05 and more preferably 1 to 0.34 to 0.04. Additional water enters the cook via the condensation of the steam that is injected into the batch cooker.

The powder that is obtained by the present example can then be used with or incorporated as an ingredient in a food intermediate. The term food "intermediate" as used herein refers to at least one intermediate that undergoes a further processing step, such as baking, mixing, etc. before the final food product is formed. In food processing, one or more intermediates may be formed. An example of a food intermediate is dough which can be used in the formation of breads, cereals, pasta, muffins, rolls and the like.

In addition to the foregoing processes, in order to control or reduce bitter flavors produced by the process, oxidation may be reduced (through the addition of ozone), the bran may be sheared during cooking or the concentration of the alkali may be changed. If the bran subsequent to treatment is too dark then the color of the bran may be bleached through the use of hydrogen peroxide. The hydrogen peroxide is believed not to have any effect on the flavor of the product.

In addition to the steps referenced in the foregoing example, fine grinding of wheat shorts or wheat bran may also be done (e.g. by using a Nisshin Engineeering Blade Mill or DPM mill) prior to the start of the process. The wheat bran is ground to a particle size of greater than 10 microns and preferably about 16 microns. Another mechanism for performing the initial separation step of the present invention is through use of a Turborotor. The grinding may or may not be performed prior to the hydrating the material.

In alternative embodiments, the bran can be processed using extrusion cooking or vacuum cooking. It has been found that these processes may improve the color of the mixture as well as allow for higher calcium hydroxide levels. Extrusion cooking may also aid in lowering costs associated with the process and further increasing the soluble fiber content of the mixture. When extrusion cooking is used, the optimal moisture content is around 30-40% or more preferably about 32% as opposed to roughly the 45-55% range, which may be needed in the batch cooker.

In a further example of the present invention, the dry ingredients (wheat bran 90-95% and calcium hydroxide 5-10%) are mixed together and then added into a cooker having a shell temperature of 70-75° F. An oxygen scavenger ingredient such as sodium bisulfite, at 0.01 to 0.10% level, may or may not be added in the mixture. The ingredients are rolled and subjected to a vacuum of −25 psig for five minutes. The ingredients are cooked for 30 minutes at a pressure of 35 psig.

After the cooking/steaming, vacuum is pulled for five minutes. After this initial period, a vacuum is pulled for an additional two minutes and cold water spray is added. The cooker is then opened and the contents discharged.

The contents are then mixed in a Hobart mixer and the bran is neutralized through the addition of citric acid while the solution is being mixed. After mixing, the bran is dried for 20 minutes for between 200-210° F., -milled by use of a Fitz mill and then dried for another 10 minutes. Once the mixture equilibrates overnight, the mixture is then ground further with a pin or disc mill.

In using the above process, the bran appeared lighter in color than in the first described process, presumably due to the reduction of Maillard browning reactions and other oxidation processes.

In vitro tests were conducted to determine the level of bile acid binding in connection with a wheat bran that had been modified in accordance with the present invention and an unmodified wheat bran. The following results were obtained and are shown in the table below.

TABLE 1

| Component % | Bile Acid Binding (% of Cholestyramine) | Viscosity at 37° C. Soluble Fiber, cP* g/cm³ |
|---|---|---|
| Unmodified White 2.7% Wheat Bran | 6.4% | 2.03 |
| Ca(OH)₂ modified 10.2% White Wheat Bran | 10.5% | 8.61 |

As table 1 illustrates, the process of the present invention improved the bile acid binding capability of the wheat bran by approximately 70% due to the increase in the level of soluble fiber and/or viscosity.

An exemplary food was prepared consisting of a ready to eat (RTE) cereals. This exemplary RTE cereal is in the form of flakes that are created by preparing a cooked cereal dough through known methods and then forming the cooked cereal dough into pellets that have a desired moisture content. The pellets are then formed into wet flakes by passing the pellets through chilled roller and then subsequently toasting or heating the wet cereal flakes. The toasting causes a final drying of the wet flakes, resulting in slightly expanded and crisp RTE cereal flakes. The flakes are then screened for size uniformity. The final flake cereal attributes of appearance, flavor, texture, inter alia, are all affected by the selection and practice of the steps employed in their methods of preparation. For example, to provide flake cereals having a desired appearance feature of grain bits appearing on the flakes, one approach is to topically apply the grain bits onto the surface of the flake as part of a coating that is applied after toasting.

The following table represents the RTE flake cereal prepared in accordance with the present example in which approximately 30% of the wheat used in the flake cereal has been replaced with the modified bran of the present invention.

TABLE 2

| Description | Standard Flake Cereal | Modified Bran Flake |
|---|---|---|
| Cereal | | |
| Total Fiber (g/serving) | 3.0 g | 5.0 g |
| Soluble Fiber (g/serving) | 0.41 g | 1.09 g |
| Calcium (w/out fortification) | 0 mg/serving | 14.4 mg/serving |

The analysis provided in table 2 above, illustrates the increased level of soluble fiber in the RTE cereal by using the modified bran of the present invention in lieu of wheat bran obtained from conventional sources.

While the foregoing example is directed to the manufacture of flake cereals, it is readily apparent, that the manufacturing method can be modified to produce puffed or extruded cereals as well in which the dough after forming is either fed through an extruder to create the desired shape or,in the alternative, is forced through a die or other orifice to generate puffed cereals.

In a study using an independent laboratory, Ca(OH)₂ modified wheat bran, obtained from the process described herein, was used in connection with a control and other diets and was fed to laboratory animals. One hundred thirty (130) hamsters were initially fed the same diet for one week. The hamsters were then randomly selected and separated into groups of 10 and were fed the test diets identified in the following table for four weeks. Blood samples were drawn from each of the animal groups and readings taken at the 3 and 4-week intervals and averages obtained. The following table shows the average blood cholesterol level taken after 4 weeks from the laboratory animals identified above.

TABLE 3

| Group/Diet | Cholesterol Levels |
|---|---|
| Control Diet | 204 |
| Unmodified wheat bran | 192 |
| Alkali modified bran | 153 |

TABLE 3-continued

| Group/Diet | Cholesterol Levels |
|---|---|
| Psyllium Diet | 145 |
| Oat Based Cereal Diet | 188 |

The study results obtained in Table 3 above reveals that through the use of the modified bran obtained in accordance with the present invention, the laboratory hamsters realized a 25% reduction in cholesterol levels. While the psyllium diet produced slightly better results, psyllium, as indicated above, suffers from other drawbacks.

In another method of the present invention, wheat shorts were obtained and the process as described above was followed except that the wheat shorts were treated with sodium hydroxide at a pH of 12.1 for one hour. The wheat shorts were then neutralized with hydrochloric acid to a pH of approximately 6.8.

In conducting a comparison of the bile acid binding properties of the wheat shorts obtained by the above mentioned process, an arabinogalactan—a soluble fiber marketed under the name LAREX available from Larex, Inc. of St. Paul, Minn. LAREX, has been shown to reduce cholesterol levels but is an expensive ingredient. The following results show the amount of bile acid binding of a sample of material prepared in connection with the invention compared with Larex (micrograms of bile acid per milligram of sample):

| Sample | Binding (% of cholestyramine) |
|---|---|
| Wheat Shorts | 12.6 |
| LAREX | 7.5 |

The wheat shorts used in the alternative embodiment after undergoing treatment according to the present invention showed a soluble fiber content of approximately 24% on a dry weight basis. The extract was obtained through centrifugation or sedimentation by known methods.

The invention should not be limited to wheat bran or wheat shorts in achieving higher soluble fiber levels. Instead, the process described in the present invention is suitable for use with any similar carbohydrate/fiber backbone such as those in corn, wheat, barley, oats, rice and portions thereof. For example, where oat hulls are used as the starting material and subjected to the same process the amount of soluble fiber contained in the extract on a dry weight basis was 16%, which represents a significant improvement over the soluble fiber content of oat hulls, which normally is in the low single digits on a dry weight basis. Corn bran, oat bran and rice bran have also been found to be suitable starting materials. In another embodiment, mixtures of two or more materials selected from the group of wheat bran, rice bran, oat bran and corn bran may be used.

It will thus be seen according to the present invention that a highly advantageous method for converting insoluble wheat fiber to soluble fiber has been provided. While the invention has been described in connection with what is presently considered to be the most practical and preferred embodiment, it will be apparent to those of ordinary skill in the art that the invention is not to be limited to the disclosed embodiment, that many modifications and equivalent arrangements may be made thereof within the scope of the invention, which scope is to be accorded the broadest interpretation of the appended claims so as to encompass all equivalent structures and products.

The invention claimed is:

1. A method of increasing soluble fiber level and viscosity of grain based material for use in food intermediates, comprising the steps of;
   providing a source of material having an initial extractable soluble fiber content of less than 4% by weight on a dry weight basis, the source comprising a dehulled bran fraction of a grain, wheat shorts or corn cobs;
   adding an alkali to said material to create a mixture;
   cooking said mixture at a pressure of 25 to 36 psig (172.4 to 248.2 kPa);
   hydrating said material;
   neutralizing said mixture;
   drying said mixture to less than 20% moisture content; and
   grinding said mixture to form a powder having an extractable soluble fiber content of greater than 8% by weight.

2. A method of increasing soluble fiber levels and viscosity of grain based materials for use in food intermediates, as recited in claim 1, wherein said alkali is selected from the group of calcium hydroxide, potassium hydroxide and sodium hydroxide.

3. A method of increasing soluble fiber levels and viscosity of grain based materials for use in food intermediates, as recited in claim 1, wherein said cooking is done for between 10 to 120 minutes.

4. A method of increasing soluble fiber levels and viscosity of grain based materials for use in food intermediates, as recited in claim 1, wherein said cooking is done at temperatures ranging from 100° C. to 140° C.

5. A method of increasing soluble fiber levels and viscosity of grain based materials for use in food intermediates, as recited in claim 1, wherein the step of neutralizing the mixture is done by adding an acid selected from the group consisting of citric acid and hydrochloric acid.

6. A method of increasing soluble fiber levels and viscosity of grain based materials for use in food intermediates, as recited in claim 1, wherein the extractable soluble fiber level of the powder is more than 10% dry weight.

7. A method of increasing soluble fiber levels and viscosity of grain based materials for use in food intermediates, as recited in claim 1, including a further step of adding the powder to a food intermediate to produce a ready to eat food product.

8. A method of increasing soluble fiber levels and viscosity of grain based materials for use in food intermediates as recited in claim 7, wherein the ready to eat foo product is cereal.

9. A method of increasing soluble fiber levels and viscosity of grain based materials for use in food intermediates as recited in claim 7, wherein the ready to eat food product is a ready to eat meal.

10. A method of increasing soluble fiber levels and viscosity of grain based materials for use in food intermediates as recited in claim 1, wherein the food intermediate is dough.

11. A method of increasing soluble fiber levels and viscosity of grain based materials for use in food intermediates as recited in claim 1, wherein the material is hydrated to a level between 30 to 100%.

12. A method of increasing soluble fiber levels and viscosity of grain based materials for use in food intermediates, as recited in claim 1, including a further step of hydrating the mixture after addition of the alkali to maintain a moisture content of approximately 40 to 60%.

13. A method of increasing soluble fiber levels and viscosity of grain based materials for use in food intermediates as recited in claim 1, including a further step after providing the source of material, the material is subjected to grinding to create a particle size of greater than 10 microns.

14. A method of increasing soluble fiber levels and viscosity of grain based materials for use in food intermediates as recited in claim 1, wherein the cooking includes steaming.

15. A method of increasing soluble fiber levels and viscosity of grain based materials for use in food intermediates as recited in claim 1, wherein after the cooking a vacuum is pulled.

16. A method of increasing soluble fiber levels and viscosity of grain based materials for use in food intermediates as recited in claim 1, wherein the cooking is done by extrusion.

17. A method of increasing soluble fiber levels and viscosity of grain based materials for use in food intermediates as recited in claim 1, wherein the source of the material is wheat bran.

18. A method of increasing soluble fiber levels and viscosity of grain based materials for use in food intermediates as recited in claim 1, wherein the source of the material is wheat shorts.

19. A method of increasing soluble fiber levels and viscosity of grain based materials for use in food intermediates as recited in claim 1, including a further step of mixing the mixture after the step of cooking.

20. A method of increasing soluble fiber levels and viscosity of grain based materials for use in food intermediates as recited in claim 1, including a further step of pulling a vacuum after the step of cooking.

21. A method for increasing soluble fiber level and viscosity in cereal based materials for use in food intermediates, comprising the steps of;

providing a source of material having an insoluble fiber source and an initial extractable soluble fiber content of less than 4% by weight on a dry weight basis;
adding alkali to said material to create a mixture;
cooking said mixture in a chamber;
pulling a vacuum in said chamber during the cooking step;
hydrating said mixture while in said vacuum;
discharging said mixture from said chamber;
mixing said mixture;
neutralizing said mixture;
drying said mixture; and
grinding said mixture into a powder so as to be able to use said powder in a food intermediate has an increased soluble fiber content of greater than 8% by weight.

22. A method of increasing soluble fiber levels and viscosity of grain based materials for use in food intermediates as recited in claim 1, wherein the source of the material is oat bran.

23. A method of increasing soluble fiber levels and viscosity of grain based materials for use in food intermediates as recited in claim 1, wherein the source of the material is rice bran.

24. A method of increasing soluble fiber levels and viscosity of grain based materials for use in food intermediates as recited in claim 1, wherein the source of the material is corn bran.

25. A method of increasing soluble fiber levels and viscosity of grain Based materials for use in intermediates as recited in claim 1, wherein the source of the material is a mixture of two or more selected from the group consisting of wheat bran, corn bran, rice bran and oat bran.

* * * * *